United States Patent
Shahid

(10) Patent No.: US 9,457,011 B2
(45) Date of Patent: Oct. 4, 2016

(54) COMPOSITIONS AND METHODS FOR THE TREATMENT OF ACID-RELATED GASTROINTESTINAL DISORDERS CONTAINING A DITHIOLANE COMPOUND AND A GASTRIC ACID SECRETION INHIBITOR

(71) Applicant: Muslim D. Shahid, Spring, TX (US)

(72) Inventor: Muslim D. Shahid, Spring, TX (US)

( * ) Notice: Subject to any disclaimer, the term of this patent is extended or adjusted under 35 U.S.C. 154(b) by 29 days.

(21) Appl. No.: 14/189,322

(22) Filed: Feb. 25, 2014

(65) Prior Publication Data

US 2015/0238463 A1    Aug. 27, 2015

(51) Int. Cl.
| | |
|---|---|
| *A61K 31/44* | (2006.01) |
| *A61K 31/435* | (2006.01) |
| *A61K 31/415* | (2006.01) |
| *A61K 31/38* | (2006.01) |
| *A61K 31/385* | (2006.01) |
| *A61K 31/4439* | (2006.01) |
| *A61K 31/341* | (2006.01) |

(52) U.S. Cl.
CPC ........... *A61K 31/385* (2013.01); *A61K 31/341* (2013.01); *A61K 31/4439* (2013.01)

(58) Field of Classification Search
None
See application file for complete search history.

(56) References Cited

U.S. PATENT DOCUMENTS

| | | |
|---|---|---|
| 3,950,333 A | 4/1976 | Durant et al. |
| 4,255,431 A | 3/1981 | Junggren et al. |
| 6,930,119 B2 | 8/2005 | Bobotas et al. |
| 7,399,772 B2 | 7/2008 | Phillips et al. |

OTHER PUBLICATIONS

Pouchain et al., Gaviscon® vs. omeprazole in symptomatic treatment of moderate gastroesophageal reflux. a direct comparative randomised trial, BMC Gastroenterology, , 12(18):1-8, 2012.*
Smith et al., Lipoic Acid as a Potential Therapy for Chronic Diseases Associated with Oxidative Stress, Current Medicinal Chemistry, 11, 1135-1146, 2004.*

* cited by examiner

*Primary Examiner* — Jeffrey S Lundgren
*Assistant Examiner* — Michael Schmitt
(74) *Attorney, Agent, or Firm* — Vincent G. LoTempio; Kloss, Stenger & LoTempio; David T. Stephenson

(57) ABSTRACT

The present disclosure describes a treatment for acid related gastrointestinal disorders. The compounds described herein are known gastric acid secretion inhibitors in combination with alpha lipoic acid (ALA) or related compounds. ALA is not known as a treatment for acid related gastrointestinal disorders, however, ALA, when combined as described in the present disclosure with certain compounds used in the treatment of acid related gastrointestinal disorders, significantly improves existing treatments.

16 Claims, No Drawings

COMPOSITIONS AND METHODS FOR THE TREATMENT OF ACID-RELATED GASTROINTESTINAL DISORDERS CONTAINING A DITHIOLANE COMPOUND AND A GASTRIC ACID SECRETION INHIBITOR

BACKGROUND OF THE INVENTION

1. Field of the Invention

The present disclosure relates to the combination of known biologically active compounds for the treatment of acid-related gastrointestinal disorders. The compounds used in the combination according to the present disclosure are known gastric acid secretion inhibitors in combination with ALA or related compounds. ALA is not known as a treatment for acid related gastrointestinal disorders, nor is it anywhere suggested that ALA would be useful for the treatment of acid-related gastrointestinal disorders, or useful for the enhancement of current treatments for acid-related gastrointestinal disorders. Unexpectedly, ALA, when combined as described in the present disclosure with certain common compounds used in the treatment of acid-related gastrointestinal disorders, has a synergistic effect in improving symptoms.

Acid-related gastrointestinal disorders include gastroesophageal reflux disease (GERD), heartburn, and gastrointestinal ulcers. GERD is a digestive disorder that affects the lower esophageal sphincter (LES), the ring of muscle between the esophagus and stomach. Doctors believe that GERD may be caused by hiatal hernia. Frequently, heartburn can be relieved through diet and lifestyle changes; however, some people may require medication or surgery.

Gastroesophageal refers to the stomach and esophagus. Reflux means to flow back or return. Therefore, gastroesophageal reflux is the return of the stomach's contents back up into the esophagus. In normal digestion, the lower esophageal sphincter (LES) opens to allow food to pass into the stomach and closes to prevent food and acidic stomach juices from flowing back into the esophagus. Gastroesophageal reflux occurs when the LES is weak or relaxes inappropriately; allowing the contents of the stomach to flow up into the esophagus. The refluxed liquid can inflame and damage the lining of the esophagus. This liquid may also contain bile that has backed-up into the stomach from the duodenum. Acid is believed to be the most harmful component of refluxed liquid. Pepsin and bile also may injure the esophagus, but their role in esophageal inflammation and damage is unclear. The severity of GERD depends on LES dysfunction, the type and amount of refluxed liquid and the neutralizing effect of saliva.

GERD is a chronic condition; once it begins, it usually is life-long. Injury to the lining resulting from GERD is also typically chronic. Moreover, after the esophagus has healed with treatment and treatment is stopped, the injury will return in most patients within a few months. Once treatment for GERD is begun, it will typically need to be continued indefinitely.

Heartburn, also called acid indigestion, is the most common symptom of GERD and usually feels like a burning chest pain beginning behind the breastbone and moving upward to the neck and throat. More than 60 million American adults experience heartburn at least once a month, and more than 15 million adults suffer daily from heartburn. Heartburn affects men, women and children alike.

The body has natural defenses against the harmful effects of acid reflux. For example, most reflux occurs during waking hours when individuals are upright. In the upright position, gravity causes the refluxed liquid to flow back down into the stomach. Further, during waking hours, individuals repeatedly swallow, regardless of reflux. Each swallow returns refluxed liquid to the stomach. In addition, saliva contains bicarbonate. With each swallow, bicarbonate-containing saliva travels down the esophagus. The bicarbonate neutralizes normal amounts of acid in the esophagus. During sleep, gravity has no in effect, swallowing stops, and the secretion of saliva is reduced. Therefore, reflux that occurs at night is more likely to result in acid remaining in the esophagus longer and causing greater damage to the esophagus.

Pharmacological medicine has established that gastroesophageal reflux disease and gastrointestinal ulcers are induced by unbalance between aggressive factors, e.g. hydrochloric acid, pepsin, and defensive factors, e.g. mucosal blood flow and mucus secretions. Therefore, it is desirous to have available some synthetic and/or natural substance that exhibits pharmacological activity of both an action of inhibiting gastric acid secretion and an action of enhancing protection of the gastric mucosa.

2. Summary of the Related Art

Standard treatment for acid-related gastrointestinal disorders involves the use of proton pump inhibitors and histamine H2 acid receptor antagonists. Both classes of drugs work by suppressing gastric acid secretion.

Proton pump inhibitors (PPI's) are compounds that suppress gastric acid secretion by the specific inhibition of the H+/K+--ATPase enzyme system (proton pump) at the secretory surface of the gastric parietal cell. Practically, over the counter (OTC) PPI's have become the mainstay in the management of gastroesophageal reflux disease (gerd) and gastric acid secretions. Common OTC drug compounds in the class of proton pump inhibitors are Omeprazole, Lansoprazole, Pantoprazole, Rabeprazole, Esomeprazole, and Zegerid. These PPI's belong to a chemical class found to be useful as gastric acid secretion inhibitors. An early patent representative of PPI's is U.S. Pat. No. 4,255,43, which teaches the use of 2-(2-benzimidazolyl)-pyridines as a method for inhibiting gastric acid secretion.

Histamine $H_2$-acid receptor antagonists were developed as drugs for the treatment of acid-peptic disease, including duodenal and gastric ulcers, gastroesophageal reflux disease and common heartburn. Histamine interaction with $H_2$ receptors in the parietal cells of the gastric mucosa results in the secretion of gastric acid. Histamine $H_2$-acid receptor antagonists compete effectively with histamine to block gastric secretions. Common histamine $H_2$-acid receptor antagonist's drug compounds include Ranitidine HCL, Cimetidine, Famotidine, and Nizatidine. An early patent representative of PPI's is U.S. Pat. No. 4,128,658, which teaches the use of aminoalkyl furan derivatives or physiological salts of N-oxide or compounds thereof, to inhibit histamine $H_2$-acid receptor antagonist's activity.

While both PPI's and histamine H2 acid receptors have been generally successful for treating acid-related gastrointestinal disorders, for many they have not been fully successful. New surveillance data on GERD patients indicates that almost half of GERD persons don't get complete relief from GERD symptoms even while taking proton pump inhibitors (PPI's), the strongest medication currently offered for gastroesophageal reflux or heartburn. Thus, it is readily apparent there exists a need for faster acting and more effective treatment regimens to better manage GERD and severe heartburn. Therefore, a means of enhancing the effects of known drugs is desired.

SUMMARY OF THE INVENTION

ALA and its metabolic derivatives are known to have pharmacological activity. Early research on ALA oral uptake suggested relatively transient and low cellular accumulation, however, recent studies have indicate ALA exhibits an array of cellular interactions from being a potent antioxidant, a strong metal chelator, to a mediator of cell signaling pathways. For the purposes of the present disclosure reference to dithiolane compounds includes ALA and its modified derivatives, which includes metabolic and synthetic derivatives. Modified derivatives, as applied to any compound in this specification may refer to metabolic or synthetic derivatives.

ALA, an organic dithiolane ring compound, is a necessary cofactor for mitochondrial α-ketoacid dehydrogenases, and thus serves a critical role in mitochondrial energy metabolism. ALA, a racemic mixture has one chiral center and therefore exists in both R- and S-enantiomeric forms. However, only R-ALA is conjugated to conserved lysine residues in an amide linkage, thus making this iso-form essential as a cofactor in biological systems.

Enantiomeric Forms of Lipoic Acid

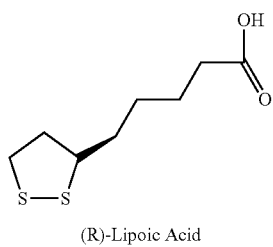

(R)-Lipoic Acid

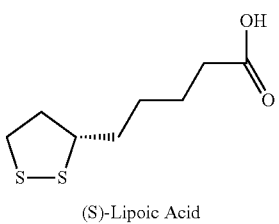

(S)-Lipoic Acid

There is growing evidence that ALA may act indirectly to maintain cellular antioxidant status by either inducing the uptake or enhancing the synthesis of endogenous low molecular weight antioxidants or antioxidant enzymes. ALA markedly increases intracellular glutathione (GSH), an abundant natural thiol antioxidant and co-substrate for detoxification enzymes, in a variety of cell types and tissues.

ALA is capable of oxidizing sulfhydryl groups and forming mixed disulfides on proteins. The multiplicative nature of signal transduction may explain some of the beneficial effects of ALA, since ALA accumulates at only micromolar levels, whereas the intracellular antioxidant GSH is present at millimolar levels.

Currently, there exist no published research studies evaluating the effect of ditholane compounds on gastroesophageal reflux disease or gastric acid secretions. Even more so, no such research publications or clinical trials have been done investigating the use of ditholane compounds and more specifically ALA combined with known pharmacological active OTC proton pump inhibitors or pharmacological active histamine $H_2$ acid receptor antagonist to treat or control gastric acid secretions or heartburn.

The present disclosure comprises (1) proton pump inhibitors (PPI's), or a histamine $H_2$-acid receptor antagonists and (2) a natural or synthetic dithiolane compound, their derivatives, and their biological metabolites thereof, and more specifically ALA, such that the present disclosure of a dithiolane compound with either (a) a pharmacological active proton pump inhibitor or (b) a pharmacological active histamine $H_2$-acid receptor antagonists is faster acting and more effective in inhibiting acid-related gastrointestinal symptoms of lower and upper chest burning, burping gastric secretion reflux, and acid regurgitations than the use of PPI's or histamine $H_2$-acid receptor antagonists alone.

DETAILED DESCRIPTION OF INVENTION

The present invention demonstrates that treatment of acid-related gastrointestinal disorders is improved with combined use of dithiolane compounds and either proton pump inhibitors or histamine H2 acid receptor antagonists. This combination may include (a) a natural or synthetic dithiolane compound having 2 to 10 carbon atoms between the two sulfur atoms, its metabolites, or derivatives thereof of the organic dithiolane ringed compound, such as Alpha-Lipoic Acid, and (b) a proton pump inhibitor like 5-methoxy-2-[(4-methoxy-3,5-dimethyl-2-pryridinyl) methyl]sulfinyl]-1H-benzimidazole, commercially known as Omeprazole, or a histamine $H_2$-acid receptor antagonists like 2-cyano-1-methyl-3-(2-[(5-methyl-1H-imidazol-4-yl) methylthio]ethyl)guanidine, commercially known as Cimetidine.

Though available from normal nutritional sources, significant amounts of ALA, with regard to the present disclosure, are not reasonably available in the typical Western diet. Dietary supplements that typically range from 50 to about 1200 mg are the primary sources of ALA, and most of the information as to ALA bioavailability comes from studies using supplements in these dosage ranges.

When given orally or intravenous in various mammals (i.e., man), the metabolism and catabolism pathways of ALA have been thoroughly elucidated. The potential biochemical and therapeutic actions, as well the understanding of ALA bioavailability is well understood. Transwell model system studies show that ALA rapidly traverses the cell monolayer in a pH-dependent manner. ALA transport was found to be inhibited medium-chain fatty acids, suggesting that the monocarboxylate transporter was the likely carrier responsible for intestinal absorption of ALA. In addition to MCT transporters, other in vitro studies identified ALA as a substrate for the $Na^+$-dependent multivitamin transporter, which may not only contribute to its gastrointestinal uptake, but also may be involved in ALA transport into tissues from the blood plasma. Thus, ALA bioavailability appears to depend upon multiple carrier proteins.

The systemic pharmacokinetics of ALA in humans is fairly rapid. ALA intestinal uptake is quickly partitioned to tissues that uptake ALA (brain, heart, and muscle) and includes a transient liver storage of ALA.

ALA is metabolized and catabolized into the following metabolites upon human absorption:

Reduction/Oxidation β-Oxidation β-Oxidation & S-Methylation

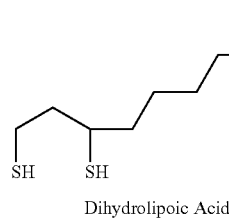

Dihydrolipoic Acid

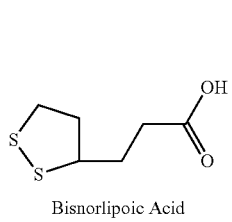

Bisnorlipoic Acid 6, 8-Bismethyl-thiooctanoic Acid

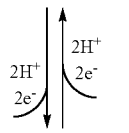

Tetranorlipoic Acid 4, 6-methylthiohexanoic Acid

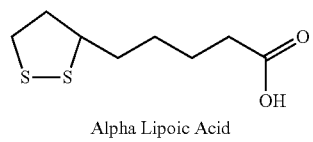

Alpha Lipoic Acid 2, 4-Bismethyl-thiobutanoic Acid

ALA and its analogs dihydrolipoic acid, bisnorlipoic acid, 6,8-bismethylthio-octanoic acid, tetranorlipoic acid, 4,6-bismethylthio-hexanoic acid, 2,4-bismethylthio-butanoic acid are contemplated as a dithiolane component for the purposes of the present disclosure.

Any dithiolane ringed compound similar in structure to ALA is contemplated as a dithiolane component for the purposes of the present disclosure. Other chemical substances that are expected to satisfy the present disclosure using would include but not be limited to the following compounds with the basic chemical structures:

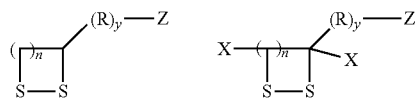

Where n is a integer from to 1 to 9, x could be but not be limited to a substituent such as alkyl, alkene, alkyne, aryl, alkylaryl, alkylaryl, (R) is $CH_2$, CHCH, y is a integer from 1 to 20, Z could be but not limited to: COOH, $COOR_1$ [where $R_1$ is: alkyl, alkene, alkyne, aryl, alkylaryl, alkylaryl, alkylphosphate, alkylphosphite, arylphospate, arylphosphite, alkylsulfate, arylsulfate, alkylarylsulfate, alkylsulfite, arylsulfite, alkylarylsulfite, arylamine, pyrimidine, imidazoline, purine, hydrogen, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl, alkylcarbamoyl, dialkylcarbamoyl, alkylcarbonylmethyl, alkoxycarbonylmethyl, and alkylsulphonyl, F, CL, Br, P, S, NO, $NO_3$, NO2, SO, $SO_2$, $NH_2$, NNH, NO3, $NO_2$, $PO_4$, $PO_3$, $POOR_2$, $POR_2R_2$, $SR_2R_2$, $SOR_2$, $NNR_2$, $NHR_2$, $NR_2R_2$ ($R_2$ is: hydrogen, alkyl, alkene, alkyne, aryl, alkylaryl, alkylaryl, alkylphosphate, alkylphosphite, arylphospate, arylphosphite, alkylsulfate, arylsulfate, alkylaryl-sulfate, alkylsulfite, arylsulfite, alkylarylsulfite, arylamine, pyrimidine, imidazoline, purine, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl, alkylcarbamoyl, dialkylcarbamoyl, alkylcarbonylmethyl, alkoxycarbonylmethyl, and alkylsulphonyl)]. The preferred organic dithiolane ringed compound is ALA.

It can be further stated that the alkali and alkali earth metal salts of ALA are included in the present disclosure. Such salts of ALA could be but not limited to NaALA, KALA, CaALA, MgALA, and SrALA. Racemic salts of ALA such a NaR-ALA, KR-ALA, NaS-ALA, and KS-ALA will also satisfy the teachings of this disclosure. However, because R-ALA is far more bio-available and bioactive than S-ALA, the preferred racemic molecule would be the salts of R-ALA.

The amount of ALA, any of its metabolites, racemic analogs, acid metal salts, or organic dithiolane compounds selected from the groups given needed to control acid-related gastrointestinal disorders for the purposes of the present disclosure could range from 1 mg to 2400 mg, preferably from 200 mg to 1800 mg, and even more preferably from 50 mg to 1200 mg per day.

The other component of the present disclosure utilizes known products currently sold as prescription or OTC drugs. Such products are classified as proton pump inhibitors or histamine $H_2$ receptor antagonists.

Some proton pump inhibitors with the spine structure

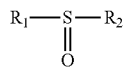

for the purposes of the present disclosure, include the following chemical structure,

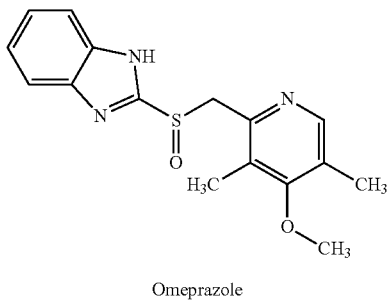 [SMILES: COc1c(C)cnc(CS(=O)c2nc3ccccc3[nH]2)c1C]

Omeprazole wherein R.sup.1 and R.sup.2 in the above structure is the same, methoxy group but could be different such as hydrogen, alkyl, halogen, carbomethoxy, carbethoxy, alkoxy, or alkanoyl, R.sup.6 is hydrogen, methyl or ethyl, R.sup.3, R.sup.4 and R.sup.5 are the same or different and are each hydrogen, methyl, methoxy, ethoxy, methoxyethoxy or ethoxyethoxy whereby R.sup.3, R.sup.4 and R.sup.5 are not all hydrogen, and whereby when two of R.sup.3, R.sup.4 and R.sup.5 are hydrogen the third of R.sup.3, R.sup.4 and R.sup.5 is not methyl. These compounds are pharmacologically active and sold as gastric acid secretion inhibitors. Other commercial prescription or OTC proton pump inhibitors included in the teaching of the present disclosure is illustrated below.

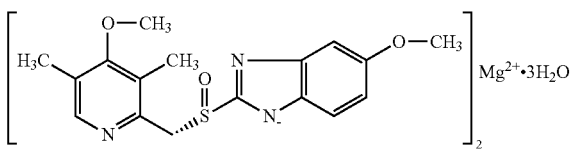

Nexium

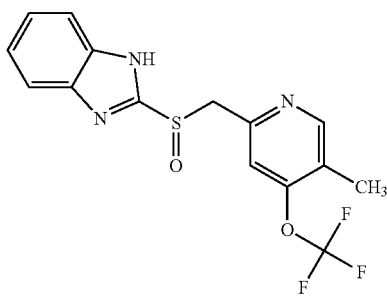

Lansoprazole

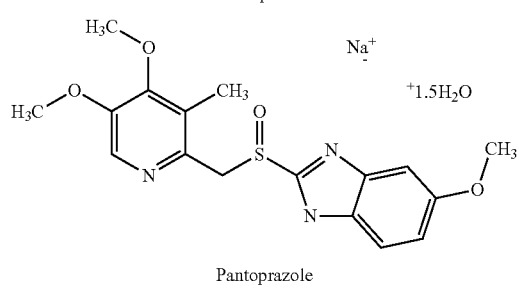

Pantoprazole

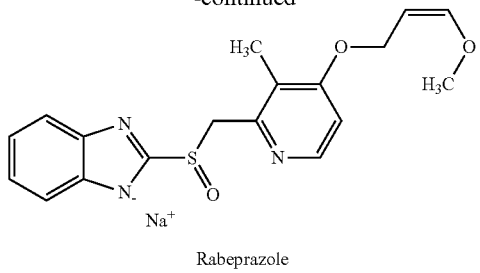

Rabeprazole

Other compounds contemplated by the present disclosure include: 2-[2-(4-methoxy)-pyridylmethylsulfinyl]-(5-acetyl-6-methyl)-benzimidazole,
2-[2-(4-methoxy)-pyridylmethylsulfinyl]-(4,6-dimethyl)-benzimidazole,
2-[2-(3,5-dimethyl-4-methoxy)-pyridylmethylsulfinyl]-(5-acetyl-6-methyl)-benzimidazole,
2-[2-(4-methoxy)-pyridylmethylsulfinyl]-(5-carbomethoxy-6-methyl)-benzimidazole,
2-[2-(4-ethoxy)-pyridylmethylsulfinyl]-(5-carbomethoxy-6-methyl)-benzimidazole,
2-[2-(3-methyl-4-methoxy)-pyridylmethylsulfinyl]-(5-carbomethoxy-6-methyl)-benzimidazole,
2-[2-(3,5-dimethyl-4-methoxy)-pyridylmethylsulfinyl]-(5-carbomethoxy-6-methyl)-benzimidazole,
2-[2-(4-methoxy-5-methyl)-pyridylmethylsulfinyl]-(5-carbomethyoxy-6-methyl)-benzimidazole,
2-[2-(3,5-dimethyl-4-methoxy)-pyridylmethylsulfinyl]-5-carbomethoxy)-benzimidazole,
2-[2-(3,5-dimethyl-4-methoxy)-pyridylmethylsulfinyl]-(5-acetyl)-benzimidazole,
2-[2-(4-methoxy-5-methyl)-pyridylmethylsulfinyl]-(5-methoxy)-benzimidazole,
2-[2-(3,5-dimethyl-4-methoxy)-pyridylmethylsulfinyl]-(5-methoxy)-benzimidazole,
2-[2-(3,5-dimethyl-4-methoxy)-pyridylmethylsulfinyl]-(5-methyl)-benzimidazole,
2-[2-(3,5-dimethyl-4-methoxy)-pyridylmethylsulfinyl]-benzimidazole,
2-[2-(3,5-dimethyl-4-methoxy)-pyridylmethylsulfinyl]-(5-chloro)-benzimidazole or a pharmaceutically acceptable salt thereof in a therapeutically effective amount.

The proton pump inhibitor dosage level in the present disclosure with the dithiolane compound ranges from 2 mg to 100 mg, but more preferably ranges from 10 mg to 20 mg.

Some histamine $H_2$ acid receptor antagonists whose basic spine structure R—S—R contemplated by the present disclosure includes the following compounds:

Compounds of the general formula above and physiologically acceptable salts thereof and N-oxides and hydrates, in which $R_1$ and $R_2$ are methyl, which may be the same or different represent hydrogen, lower alkyl, cycloalkyl, lower alkenyl, aralkyl or lower alkyl interrupted by an oxygen atom or a group,

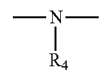

in which $R_4$ represents hydrogen or lower alkyl or $R_1$ and $R_2$ may, together with the nitrogen atom to which they are attached, form a heterocyclic ring which may contain other heteroatoms selected from O and

$R_3$ is hydrogen, lower alkyl, lower alkenyl or alkoxyalkyl; X is —$CH_2$—, O or S; Y represents =S, =O, =$NR_5$ or =$CHR_6$; Alk denotes a straight or branched alkylene chain of 1 to 6 carbon atoms; $R_5$ is H, nitro, cyano, lower alkyl, aryl, alkylsulphonyl, or arylsulphonyl; $R_6$ represents nitro, arylsulphonyl or alkylsulphonyl; M is an integer from 2 to 4; and N is 1 or 2; or when X=S, or —$CH_2$—, n is zero, 1 or 2. These compounds have been shown to exhibit histamine $H_2$-antagonist activity. Intermediates in the production thereof are also provided. Other commercially sold OTC histamine $H_2$-acid antagonist that would be included in the teaching of the present disclosure is illustrated below.

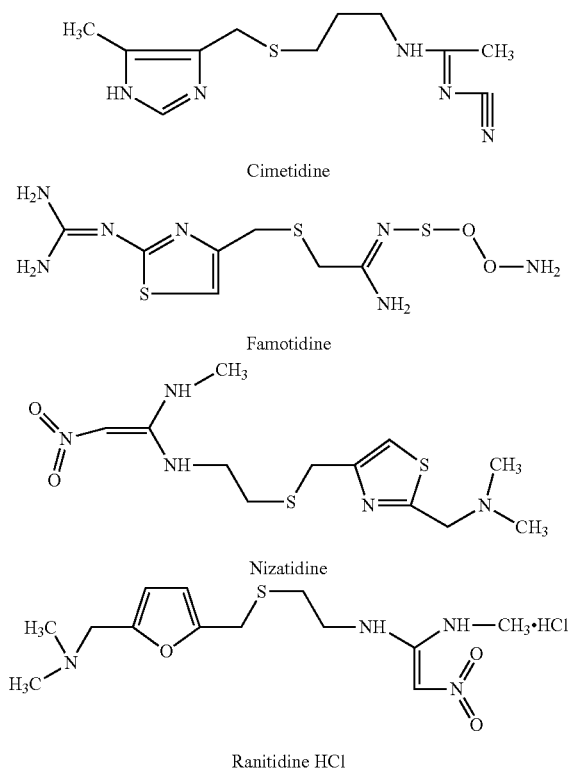

Other compounds of the present disclosure would be but not limited to the following:
-[2-[[[5-(dimethylamino)methyl-2-furanyl]methyl]thio]-ethyl]-N'-methylthiourea
N-cyano-N'-[2-[[[5-(dimethylamino)methyl-2-furanyl]methyl]thio]ethyl]-N''-methylguanidine
N-[2-[[[5-(dimethylamino)methyl-2-furanyl]methyl]thio]ethyl]-N'-methyl-2-nitro-1,1-ethenediamine
N-cyano-N'-[2-[[[5-(methylamino)methyl-2-furanyl]methyl]thio]-ethyl]-N''-methylguanidine
N-[2-[[[5-(diethylamino)methyl-2-furanyl]methyl]thio]ethyl]-N'-methyl-2-nitro-1,1-ethenediamine
N-[2-[[[5-(dimethylamino)methyl-2-furanyl]methyl]thio]ethyl]-N'-(2-methoxyethyl)-2-nitro-1,1-ethenediamine
N-[2-[[[5-(methylamino)methyl-2-furanyl]methyl]thio]ethyl]-N'-methyl-2-nitro-1,1-ethenediamine
N-[3-[[5-(dimethylamino)methyl-2-furanyl]thio]propyl]-N'-methyl-2-nitro-1,1-ethenediamine
N-[2-[[[5-(ethylmethylamino)methyl-2-furanyl]methyl]thio]ethyl]-N'-methyl-2-nitro-1,1-ethenediamine
N-[2-[[[5-(dimethylamino)methyl-2-furanyl]methyl]thio]ethyl]-N'-nitroguanidine
N-[2-[[[5-(dimethylamino)methyl-2-furanyl]methyl]thio]ethyl]-N'-methanesulphonyl-N''-methylguanidine
N-[4-[5-(dimethylamino)methyl-2-furanyl]butyl]-N'-methyl-thiourea
N-benzenesulphonyl-N'-[2-[[[5-(dimethylamino)methyl-2-furanyl]-methyl]thio]ethyl]-N''-methylguanidine
N-[5-[5-(dimethylamino)methyl-2-furanyl]pentyl]-N'-methyl-2-nitro-1,1-ethenediamine
N-cyano-N'-[5-[5-(dimethylamino)methyl-2-furanyl]pentyl]-N'-methylguanidine
N-[4-[5-(dimethylamino)methyl-2-furanyl]butyl]-N'-methyl-2-nitro-1,1-ethenediamine
N-cyano-N'-[4-[5-(dimethylamino)methyl-2-furanyl]butyl]-N''-methylguanidine
N-[2-[[[5-[3-[dimethylamino]propyl]-2-furanyl]methyl]thio]-ethyl]-N'-methyl-2-nitro-1,1-ethenediamine
N-[2-[[[5-[[2-(dimethylamino)ethyl]amino]methyl-2-furanyl]methyl]thio]ethyl]-N'-methyl-2-nitro-1,1-ethenediamine These compounds used in the present disclosure readily form physiologically acceptable salts. Such salts include salts with inorganic and organic acids such as hydrochlorides, hydrobromides and sulphates. Particularly useful salts of organic acids are formed with aliphatic mono- or di-carboxylic acids. Examples of such salts are acetates, maleates and fumarates. The compounds may also form hydrates. As indicated the compounds of the disclosure also include N-oxides, where $R_1$ and $R_2$ are both other than hydrogen. The histamine $H_2$-acid receptor antagonist dosage levels in the present disclosure range from 20 mg to 750 mg, but more preferably from 75 mg to 300 mg.

In clinical use the combination of the dithiolane, proton pump inhibitor, or the histamine $H_2$-acid receptor antagonist compounds of the disclosure are administered orally, rectally or by injection in the form of a pharmaceutical preparation which contains an active component of each as a pharmaceutically acceptable, non-toxic acid addition salt, such as hydrochloride, lactate, acetate, sulfamate, in combination with a pharmaceutically acceptable carrier. The carrier may be in the form of a solid, semisolid or liquid diluent, or a capsule. Dosage forms include: liquid, powder, tablet, capsule, effervescent powder, effervescent tablet, pellets, and granules. These pharmaceutical preparations are a further object of the disclosure. Usually the amount of active compound could range from 0.01 to 95% by weight each of the preparation, between 0.05 to 20% by weight in preparations for injection and between 0.1% and 50% by weight in preparations for oral administration. Generally, the range of oral dosage intake of the dithiolane and the proton pump is as follows:
ALA 10 mg-1200 mg, preferable 50 mg-600 mg
Omeprazole 5 mg-50 mg, preferably 20 mg-40 mg
Generally, the range of oral dosage intake of the dithiolane and histamine $H_2$-acid receptor antagonists is as follows:
ALA 10 mg-1200 mg, preferably 50 mg-600 mg
Histamine antagonists 50 mg-600 mg, preferably 75 mg-300 mg Example 1

A middle aged male subject diagnosed with GERD had been on the proton pump inhibitor omeprazole for approximately three years. The subject reported taking 40 mg of omeprazole per day to control symptoms of GERD. On a scale of 1-10, subject rated the effectiveness of omeprazole at 5. Potential factors influencing the effectiveness rating included (1) two days are required for the drug to take effect, and (2) subject consumed symptom inducing foods including peanut butter and spicy meats, resulting in mild to severe GERD even while taking appropriate oral dosages of omeprazole daily.

In accordance with the present disclosure, he began taking orally 20 mg of omeprazole and 400 mg of ALA on a daily basis. Subject reported that this combination regime completely stopped upset stomach, heartburn, and acid reflux attacks regardless of the type of foods consumed. Subject rated effectives of regime of the present disclosure a 9 on a scale from 1-10. Further evaluations with varied dosages of omeprazole and ALA further demonstrated that the combination of the present disclosure is effective for the suppression of GERD symptoms.

Additional study was undertaken to see to what extent the combination of proton pump inhibitor and ALA of the present disclosure would have on GERD and heartburn symptoms. The person was instructed to orally take 20 mg of omeprazole and 600 mg of ALA daily for 3 months. From this report it was noted that taking the combination of proton pump inhibitor and ALA at least 60 minutes (A 3-week study during the three month period was done to arrive at the conclusions) before eating resulted in the best pharmacological observed effect. The participant reported complete relief from GERD symptoms and heartburn (R=10/10). Other important facts were gathered from this 3-month study. The treatment regime is fast acting and generally will halt the symptoms of even the worst scenario of acid reflux in no more than 120 minutes. Continued relief is experienced for a minimum of 24 hours with no further oral intake of the combination regime. The participant reported eating regular foods with no more modified diet schemes. Foods such as pizza, spaghetti, chili, ice cream, pastrami, taco salads and the like, all once avoided, are now capable of being enjoyed at meal times. Further, studies with this participant demonstrated that even after GERD symptoms were present, the oral intake of 20 mg omeprazole and 600 mg of ALA will begin to sequester GERD symptoms in about 30 minutes, with complete inhibition of GERD symptoms around 60 to 120 minutes after oral consumption of combination regime of the present disclosure.

Example 2

An 18 yr-old female subject who had been diagnosed with moderate acid reflux by her personal physician was prescribed 20 mg Nexium per day. However, due to cost she has been on one to two 20 mg OTC omeprazole (OMP) per day. She has reported only marginal relief from heartburn and GERD while taking omeprazole daily After taking orally 20 mg omeprazole and 600 mg ALA one hour before eating, she consumed a homemade spaghetti dish, well-seasoned with various spices (garlic, pepper, onions), a food item from which previously avoided. After the meal the female participant experienced no acid reflux incidents while awoke or during sleeping at night. The next day, almost 24 hours later with no further oral uptake of the OMP/ALA combination regime she ate another portion of the spaghetti meal and no signs of acid reflux symptoms emerged again either awake or during resting.

The participant noted than when she ate pepperoni pizza this food item gave her the greatest discomfort and GERD incidents always occurred even while taking omeprazole. To evaluate the effect of the combination regime she took 20 mg OMP/600 mgALA one hour before eating pepperoni pizza. The female participant reported no acid reflux issues or any upper chest discomfort, such as heartburn. She did indicate an hour or so after finishing her pizza meal she burped once with a taste of pizza. No GERD symptoms occurred while awoke or while sleeping (resting). Participant gave the OMP/ALA a 9++/10 rating while giving the OTC omeprazole a 5+ rating.

Example 3

In a third subject ALA was studied to evaluate the effectiveness of the present disclosure. Subject reported that 150 mg of the histamine $H_2$-acid receptor antagonist Ranitidine HCl recommended dosage level was effective with 600 mg ALA with moderate eating in general. However, subject noted that the consumption of raw garlic, onions, pepperoni, and foods that contain spices like curry led to slight but noticeable heartburn, in the area of the upper middle chest commonly identified as the solar plexus, a few hours after consumption of these spicy foods. Interestingly, when participant took an additional 150 mg tablet of the Ranitidine HCl the symptoms of heartburn begin to dissipate over the next 2 to 3 hours. The subject rated the $H_2$-antagonist/ALA combination treatment 9.5/10. These observations suggest that high dosage levels of 300 mg or greater of the histamine $H_2$-acid receptor antagonist Ranitidine HCL with 600 mg of ALA was effective in eliminating heartburn or GERD symptoms.

The following conclusions can be reported on the use of the combination regime using a dithiolane compound, particularly ALA and/or a proton pump inhibitor or histamine $H_2$-acid receptor antagonists:

At least oral dosages of 10 mg to 40 mg of Omeprazole and oral dosages of the natural antioxidant ALA at levels of 100 mg to 1200 mg (preferably 600 mg) is an effective combination to stop heartburn and GERD. Oral dosages, preferably, of 150 mg to 300 mg of histamine $H_2$-acid receptor antagonist and, preferably, oral dosages of 600 mg of ALA are effective for controlling and stopping heartburn and gastroesophageal reflux symptoms.

The combination regimes detailed in the present disclosure, taken orally, will stop GERD symptom after full onset of GERD symptoms. The omeprazole/ALA combination shows almost complete elimination of GERD symptoms in a time period from 1 to 2 hours as compared to Omeprazole which takes on the average 2 days.

Based on the experiments related to the present disclosure, the most effective time to consume combination regimes is early in the morning at least 1 hour before food consumption or 2 to 3 hours before sleep (in order to stop resting gastric reflux episodes).

Depending upon the individual or foods consumed (sauces, spices, sugary drinks, pizza) the combination treatment may have to be taken twice daily to prevent any formation of heartburn or GERD. The effect of the combination treatment appears to last 2 days before repeated oral intake. Once use of the Omeprazole/ALA regime is terminated, the passage of four days generally will result in the reoccurrence of GERD symptoms, especially when foods such as sauces, dairy, and spices are consumed.

The scope of this disclosure should be determined by the appended claims and their legal equivalents. Therefore, it will be appreciated that the scope of the present disclosure fully encompasses other embodiments. In the present disclosure, reference to an element in the singular is not intended to mean "one and only one" unless explicitly so stated, but rather "one or more." All structural, chemical, and functional equivalents to the elements of the above-described preferred embodiment(s) are incorporated herein by reference and are intended to be encompassed by the present claims.

I claim:

1. A method of treating acid related gastrointestinal disorders comprising:
    administering orally at an effective daily dose a mixture of between 100 mg and 1500 mg of a dithiolane compound and/or one or more modified derivatives thereof, and a between 5 and 50 mg of a proton pump inhibitor and/or one or more modified derivatives thereof.

2. The method of claim 1 wherein the dithiolane compound and/or one or more modified derivatives thereof and the proton pump inhibitor and/or one or more modified derivatives thereof are orally administered prior to consuming food.

3. The method of claim 1 wherein the dithiolane compound and/or one or more modified derivatives thereof and the proton pump inhibitor and/or one or more modified derivatives thereof is administered such that a significant amount of the dithiolane compound and/or one or more modified derivatives thereof and the proton pump inhibitor and/or one or more modified derivatives thereof are able to exert a significant biological effect in the body.

4. The method of claim 1 wherein the dithiolane compound and/or one or more modified derivatives thereof and the proton pump inhibitor and/or one or more modified derivatives thereof are combined prior to administration.

5. The method of claim 4 wherein the dithiolane compound and/or one or more modified derivatives thereof and the proton pump inhibitor and/or one or more modified derivatives thereof are combined in pill form, liquid form or related means of oral ingestion.

6. The method of claim 1 wherein the dithiolane compound is 1, 2-dithiolane-3-pentanoic acid and/or one or more modified derivatives thereof.

7. The method of claim 1 wherein the dithiolane compound is the R enantiomer of 1, 2-dithiolane-3-pentanoic acid with the structure

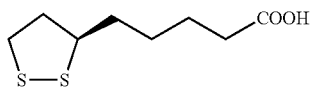 [SMILES: O=C(O)CCCC[C@@H]1CCSS1]

and/or one or more modified derivatives thereof.

8. The method of claim 1 wherein the dithiolane compound is selected from the group consisting of 1,2 dithiolane, 1,3 dithiolane, 1,4 dithiolane, and 1,5 dithiolane, and 1,6 dithiolane, 1, 2-dithiolane-3-pentanoic acid, dihydrolipoic acid, bisnorlipoic acid, 6,8-bismethylthio-octanoic acid, tetranorlipoic acid, 4,6-bismethylthio-hexanoic acid, and 2,4-bismethylthio-butanoic acid.

9. The method of claim 6 wherein said 1, 2-dithiolane-3-pentanoic acid and/or one or more modified derivatives thereof includes an alkali metal or alkaline-earth metal salt of 1, 2-dithiolane-3-pentanoic acid.

10. The method of claim 1, wherein the dithiolane compound is represented by formula I or II,

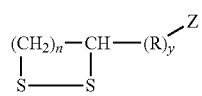

I

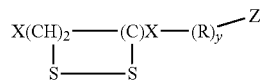

II wherein, n is an integer from to 1 to 9; wherein X is an alkyl, alkene, alkyne, aryl, alkylaryl or alkylaryl; wherein (R) is CH2 or CHCH; wherein y is an integer from 1 to 20; wherein Z is COOH or COOR1; wherein R1 is an alkyl, alkene, alkyne, aryl, alkylaryl, alkylaryl, alkylphosphate, alkylphosphite, arylphospate, arylphosphite, alkylsulfate, arylsulfate, alkylarylsulfate, alkylsulfite, arylsulfite, alkylarylsulfite, arylamine, pyrimidine, imidazoline, purine, hydrogen, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl, alkylcarbamoyl, dialkylcarbamoyl, alkylcarbonylmethyl, alkoxycarbonylmethyl, alkylsulphonyl, F, CL, Br, P, S, NO, NO3, NO2, SO, SO2, NH2, NNH, NO3, NO2, PO4, PO3, POOR2, POR2R2, SR2R2, SOR2, NNR2, NHR2, or NR2R2; wherein R2 is hydrogen, alkyl, alkene, alkyne, aryl, alkylaryl, alkylaryl, alkylphosphate, alkylphosphite, arylphospate, arylphosphite, alkylsulfate, arylsulfate, alkylarylsulfate, alkylsulfite, arylsulfite, alkylarylsulfite, arylamine, pyrimidine, imidazoline, purine, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl, alkylcarbamoyl, dialkylcarbamoyl, alkylcarbonylmethyl, alkoxycarbonylmethyl, or alkylsulphonyl.

11. The method of claim 1 wherein said proton pump inhibitor is selected from the group consisting of omeprazole, esomeprazole, lansoprazole, raveprazole and pantoprazole.

12. The method of claim 1 wherein the proton pump inhibitor is a benzimidazole compound and/or one or more modified derivatives thereof.

13. The method of claim 12 wherein the benzimidazole compound and/or one or more modified derivatives thereof is selected from a group consisting of omeprazole, 5-methoxy-2-[(4-methoxy-3,5-dimethyl-2-pryridinyl) methyl]sulfinyl]-1H-benzimidazole, Rabeprazole (RS)-2-([4-(3-methoxypropoxy)-3-methylpyridin-2-1]methylsulfinyl)-1H-benzo[d]imidazole, and Lansoprazole, (RS)-2-([3-methyl-4-(2,2,2-trifluoroethoxy)pyridin-2-yl] methylsulfinyl-1H-benzo[d]imidazole, Nexium, Lansoprazole, Pantoprazole, Rabeprazole, 2-[2-(4-methoxy)-pyridylmethylsulfinyl]-(5-acetyl-6-methyl)-benzimidazole, 2-[2-(4-methoxy)-pyridylmethylsulfinyl]-(4,6-dimethyl)-benzimidazole, 2-[2-(3,5-dimethyl-4-methoxy)-pyridylmethylsulfinyl]-(5-acetyl-6-methyl)-benzimidazole, 2-[2-(4-methoxy)-pyridylmethylsulfinyl]-(5-carbomethoxy-6-methyl)-benzimidazole, 2-[2-(4-ethoxy)-pyridylmethylsulfinyl]-(5-carbomethoxy-6-methyl)-benzimidazole, 2-[2-(3-methyl-4-methoxy)-pyridylmethylsulfinyl]-(5-carbomethoxy-6-methyl)-benzimidazole, 2-[2-(3,5-dimethyl-4-methoxy)-pyridylmethylsulfinyl]-(5-carbomethoxy-6-methyl)-benzimidazole, 2-[2-(4-methoxy-5-methyl)-pyridylmethylsulfinyl]-(5-carbomethyoxy-6-methyl)-benzimidazole, 2-[2-(3,5-dimethyl-4-methoxy)-pyridylmethylsulfinyl]-5-carbomethoxy)-benzimidazole, 2-[2-(3,5-dimethyl-4-methoxy)-pyridylmethylsulfinyl]-(5-acetyl)-benzimidazole, 2-[2-(4-methoxy-5-methyl)-pyridylmethylsulfinyl]-(5-methoxy)-benzimidazole, 2-[2-(3,5-dimethyl-4-methoxy)-pyridylmethylsulfinyl]-(5-methoxy)-benzimidazole, 2-[2-(3,5-dimethyl-4-methoxy)-pyridylmethylsulfinyl]-(5-methyl)-benzimidazole, 2-[2-(3,5-dimethyl-4-methoxy)-pyridylmethylsulfinyl]-benzimidazole, and 2-[2-(3,5-dimethyl-4-methoxy)-pyridylmethylsulfinyl]-(5-chloro)-benzimidazole.

14. The method of claim 1 wherein the dithiolane compound and/or one or more modified derivatives thereof is administered between 300 mg and 600 mg, and wherein the proton pump inhibitor and/or one or more modified derivatives thereof is administered between 10 mg and 30 mg.

15. The method of claim 1 wherein the dithiolane compound and/or one or more modified derivatives thereof and the gastric acid secretion proton pump inhibitor and/or one or more modified derivatives thereof are orally administered after consuming food.

16. A method of treating acid related gastrointestinal disorders comprising:
   administering a therapeutically effective amount of a mixture of a dithiolane compound and/or one or more modified derivatives thereof, and a proton pump inhibitor and/or one or more modified derivatives thereof.

\* \* \* \* \*